United States Patent [19]

Mastrocola et al.

[11] 4,166,061

[45] Aug. 28, 1979

[54] USE OF CYCLIC ESTERS TO PREPARE 2,3-DICHLORO-4-(2-THENOYL)PHENOXYACETIC ACID

[75] Inventors: Antonietta R. Mastrocola, Ardmore; Robert L. Webb, West Chester, both of Pa.

[73] Assignee: SmithKline Corporation, Philadelphia, Pa.

[21] Appl. No.: 847,969

[22] Filed: Nov. 2, 1977

[51] Int. Cl.$^2$ .................... C07D 333/24; C07D 333/38
[52] U.S. Cl. .................................. 549/72; 549/60; 568/649; 568/656; 260/340.2
[58] Field of Search ............... 260/332.2 A, 332.3 C, 260/332.2 R, 332.2 H

[56] References Cited

U.S. PATENT DOCUMENTS 3,758,506   9/1973   Godfroid et al. ............. 260/332.2 A

OTHER PUBLICATIONS

Morrison & Boyd, "Organic Chemistry", pp. 625–626, 673, 680–681, (3rd edition), 1974.
G. Thuillier et al., Eur. J. Med. Chem. 9(6), pp. 625–633, (1974).
Neller, "Chemistry of Organic Compounds", 3rd ed., pp. 107, 818, (1965).

*Primary Examiner*—Gerald A. Schwartz
*Attorney, Agent, or Firm*—William H. Edgerton

[57] ABSTRACT

A new process and intermediates for preparing 2,3-dichloro-4-(2-thenoyl)phenoxyacetic acid (ticrynafen, a diuretic agent) using as a key reaction a Friedel-Crafts acylation of an esterified 3-(2,3-dichlorophenoxy)-1,2-propanediol using a thenoyl halide.

7 Claims, No Drawings

USE OF CYCLIC ESTERS TO PREPARE 2,3-DICHLORO-4-(2-THENOYL)PHENOXYACETIC ACID

This invention comprises a new process for preparing 2,3-dichloro-4-(2-thenoyl)phenoxyacetic acid (ticrynafen) which is a useful diuretic agent. The process makes use of certain novel cyclic esters and diols.

PRIOR ART

Ticrynafen has been prepared using a synthetic route which includes running a Friedel-Crafts condensation with thenoyl chloride before the O-C-C skeleton of the oxyacetic acid side chain is built up. [U.S. Pat. No. 3,758,506 and G. Thuillier et al., Eur. J. Med. Chem. 9(6) 625, (1974)]. Of the novel intermediates which are a part of this invention, to the best of our present knowledge the closest art is as follows: For 3-(2,3-dichlorophenoxy)-1,2-propandiol; the 2,4-isomer, B. J. Ludwig, J. Am. Chem. Soc. 74, 1935 (1952); the 2,6-isomer, French Pat. No. 2,056,296; the 3,4-isomer, B. R. Baker, J. Med. Chem. 14 793, 1971. For the cyclic carbonates: the 2-monochloro, U.S. Pat. No. 3,168,525 and many others; the 4-monochloro, Y. M. Beasley, J. Pharm. Pharmacol. 9 10 (1956).

The present invention in its preferred aspect overall is represented by the following:

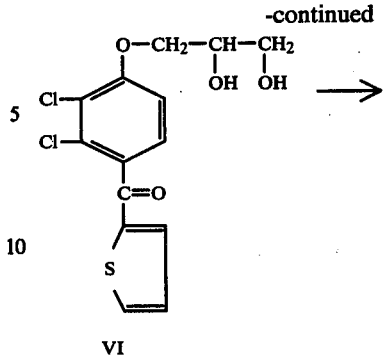
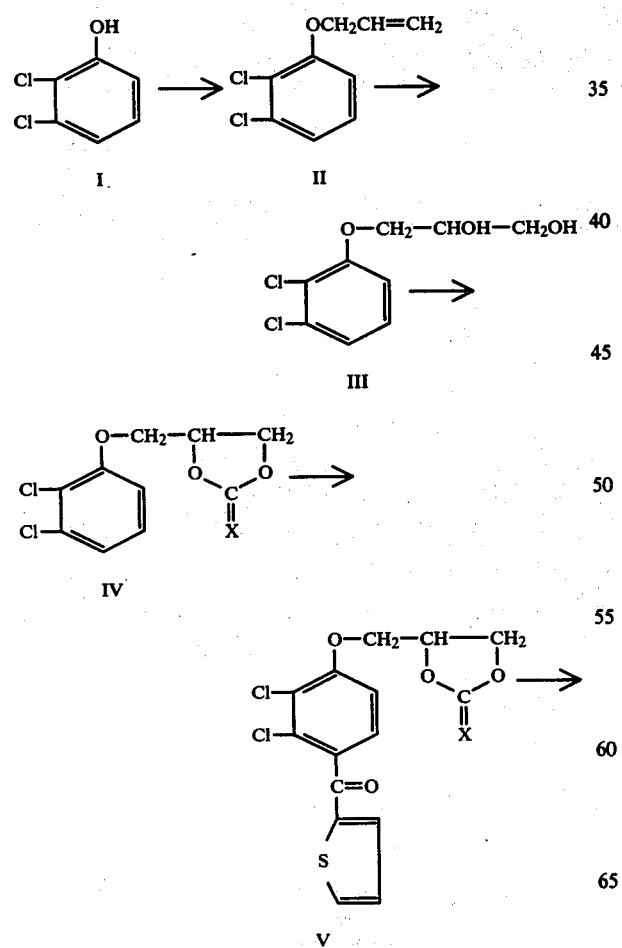
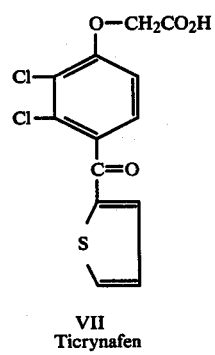

In this procedure, X is thio (=S) or preferably oxo (=O). The key step of the synthetic sequence is the Friedel-Crafts reaction involving IV→V. The novel aspects of the overall process run from III→VIII.

The novel intermediates of this invention are those of the following formula:

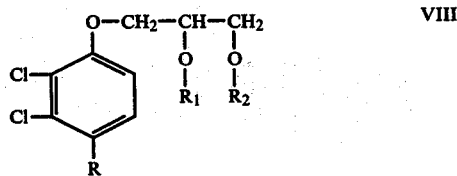

in which $R_1$ and $R_2$ are both hydrogen or, when taken together, carbonyl

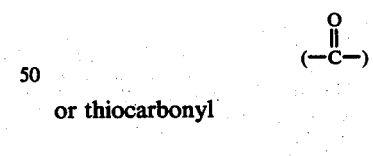

or thiocarbonyl and R is thenoyl or hydrogen. Preferred are the compounds of Formula VIII in which R is thenoyl ($C_4H_3SCO-$) and $R_1$ and $R_2$ are hydrogen, and, when taken together, carbonyl or thiocarbonyl.

The first step in this synthesis (III→IV) comprises the esterification of the two hydroxyl groups of 3-(2,3-dichlorophenoxy)-1,2-propandiol (III) to protect them from reaction during the subsequent Friedel-Crafts acylation step. This is accomplished by any standard O-acylation reaction known to the art such as using, for example, an acyl halide or anhydride. In fact any open chain ester group may be formed and used with similar but less desirable results such as the O-lower alkylcarbonyl

O-carbomethoxy

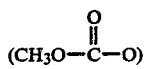

or O-carbethoxy

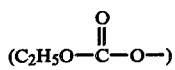

ester in which the "lower alkyl" ($R_3$) is for convenience limited to up to 5 carbon atoms such as the formate, acetate or propionate derivatives.

In fact the cyclic esters, the thiocarbonate and especially the carbonate shown, for Compounds IV are preferred since they are readily crystalline and are prepared in good yields. The cyclic carbonate is obtained very readily by reacting 3-(2,3-dichlorophenoxy)-1,2-propanediol (III) with an excess dimethyl or diethyl carbonate preferably in the presence of an alkali metal base such as sodium or potassium bicarbonate or carbonate. Most conveniently the reaction mixture is heated at reflux for from 2–6 hours. The crystalline carbonate (IV) is isolated and purified by methods known to the art. Alternatively phosgene or thiophosgene can be used in an inert organic solvent. Also lower alkyl chloroformates may be used.

The second step of this synthesis (IV→V) is the novel Friedel-Crafts acylation which involves reaction of thenoyl chloride with the esterified diol under standard Friedel-Crafts conditions. We have unexpectedly found however that using one mole equivalent of a Friedel-Crafts catalyst, such as the common Lewis acids most conveniently aluminum chloride, does not induce acylation. An excess over one mole equivalent preferably 3–5 mole equivalents gives excellent yields of the desired ester, such as 3-[2,3-dichloro-4-(2-thenoyl)-phenoxyl]-propanediol-1,2-carbonate. We have also found the nature of the alkoxy substituent on the transition state carbonium ion is critical to the efficiency of the acylation and to the p-direction of the incoming acyl group.

In the esterified carbonium donors of the Friedel-Crafts reaction the esterified starting materials, especially the preferred cyclic carbonate, give good yields of the desired isomer.

The most advantageous reaction conditions are reacting the ester with about 4 mole equivalents of aluminum chloride in methylene chloride at from room temperature up to reflux temperature until the reaction is complete, for example from 1–12 hours. The reaction product is isolated if desired by standard isolation procedures.

The third step of the synthesis (V→VI) involves removal of the protective ester groups most readily using mild acid or preferably alkaline hydrolysis conditions by methods known to the art. The fourth step of the reaction (VI→VII) comprises oxidation of the propane diol side chain of 3-[2,3-dichloro-4-(2-thenoyl)-phenoxy]propanediol-1,2. The oxidation is accomplished using any oxidizing agent capable of converting a 1,2-propylene diol moiety into the acetic acid congener without affecting the thiophene ring. The preferred conditions are chromic acid in acetic acid at from room temperature to about 75° until the reaction is complete. Other oxidation agents which may be used to give ticrynafen are permanganate, manganese dioxide, iodate/permanganate, catalytic oxidation such as using cobalt acetate or noble metal catalysts.

The esters (V) can also be converted directly to ticrynafen by oxidation without hydrolysis, to data in our hands in low yield. For example, the cyclic carbonate gives ticrynafen upon reaction with chromic acid at steam bath temperatures. Also, the reaction products of the individual steps of the synthesis outlined above may be either isolated and purified or used as such at the option of the operator. The product of the hydrolysis (V→VI) for example need not be isolated.

Using the reaction sequence described herein gives the diuretic ticrynafen (tienilic acid) in good yield with relatively inexpensive chemicals and with no undesirable environmental hazards. Of course the key intermediate (IV) which is the starting material for the Friedel-Crafts acylation may be prepared by alternative synthetic routes but with little practical advantage over that described herein.

The following examples are designed to illustrate this reaction. All temperatures are in degrees Centigrade.

EXAMPLE 1

A mixture of 652 g (4.0 m) of 2,3-dichlorophenol, 483.52 g of (4.0 m) of allyl bromide and 1 L of methanol was reacted with a mixture of 914.4 ml (4.0 m) of 25% sodium methoxide/methanol in 1 L of methanol. The mixture was heated at reflux until a t.l.c. analysis (chloroformmethanol 95:5) indicated reaction was substantially complete, about 8–10 hours.

The mixture was cooled to 30° and poured into 5 L. of water. Extraction with ether followed by washing, drying and evaporation of the extracts gave 698.15 g of crude 3-(2,3-dichlorophenoxy)-propene.

EXAMPLE 2

To a solution of 25.5 g (0.125 m) of 3-[2,3-dichlorophenoxy]propene in 150 ml of 97% formic acid was added 24 g (0.211 m) of 30% hydrogen peroxide. The mixture was allowed to stir at ambient temperature for 18 hours at which time the reaction mixture was homogeneous. The solution was diluted to 1 L with water, and the solid collected. The solid was dissolved in 200 ml of ethanol containing 21.1 g of potassium hydroxide in 21 ml water and heated under reflux for 2 hours. After ethanol had been removed from the reaction mixture under reduced pressure, the residue was diluted with water and extracted with ether. Evaporation of the dried ether gave 27 g crude 3-[2,3-dichlorophenoxy]-1,2-propandiol. Recrystallization from 60 ml of chloroform gave 22.3 g (75%) of diol m.p. 98°–100°: IR (nujol) 3400 cm$^{-1}$; NMR (DMSO-$d_6$) δ 3.5 (t, 2H), 3.7–4.1 (m, 3H), 4.7 (t, 1H), 5.0 (d, 1H), 7.2 (m, 3H); m/e 236.

Anal: Calculated for $C_9H_{10}Cl_2O_3$: C, 45.61; H, 4.25; Cl, 29.91. Found: C, 45.61; H, 4.21; Cl, 29.54.

EXAMPLE 3

22.33 g (0.0918 m) of the diol from Example 2 was dissolved in 90 ml of diethyl carbonate and to it added 0.5 g of sodium bicarbonate. The mixture was heated under reflux for six hours. On cooling, the mixture deposited needles of 3-[2,3-dichlorophenoxy]-propanediol-1,2-carbonate (17.4 g, 70%, m.p. 108°–110°) which were collected and used in the next step without further purification: IR (nujol) 1760 cm$^{-1}$; NMR (DMSO-d$_6$) δ 4.3–4.8 (m, 4H), 5.2 (m, 1H), 7.2 (m, 3H); m/e 262. A sample was recrystallized from isopropanol for analysis.

Anal: Calculated for $C_{10}H_8Cl_2O_4$: C, 45.66; H, 3.07; Cl, 26.95. Found: C, 45.46; H, 3.24; Cl, 26.72.

EXAMPLE 4

Fifty grams (0.19 m) of the ester from Example 3 was dissolved in 420 ml of methylene chloride and to it added 30.6 g (0.21 m) of 2-thiophenecarboxylic acid (thenoyl) chloride. Aluminum chloride (111.5 g, 0.84 m) was added to the reaction mixture over a period of 1 hour. The reaction mixture was heated under reflux for 1 hour, cooled, quenched with water, and heated again for 1 hour. The methylene chloride layer was separated, washed with water, 10% sodium hydroxide and water. Evaporation of the dried organic layer gave 61.8 g (59%) of crude 3-[2,3-dichloro-4-(2-thenoyl)-phenoxy]-propanediol-1,2-carbonate. Recrystallization from ethyl acetate gave 46.3 g, m.p. 125°: IR (nujol) 1800, 1660 cm$^{-1}$; NMR (DMSO-d$_6$) δ 4.6 (m, 4H), 5.3 (m, 1H), 7.5 (m, 4H), 8.2 (d, 1H); m/e 372.

Anal: Calculated for $C_{15}H_{10}Cl_2O_5S$: C, 48.27; H, 2.70; Cl, 19.00; S, 8.59. Found: C, 48.39; H, 2.89; Cl, 18.74; S, 8.41.

EXAMPLE 5

The Friedel-Crafts product from Example 4 (51 g, 0.135 m) was suspended in 300 ml of 10% sodium hydroxide and heated on the steam bath for 1 hour. The cooled reaction mixture was filtered, and washed with water to give 35 g (75%) of crude 3-[2,3-dichloro-4-(2-thenoyl)-phenoxy]-propanediol. The solid was treated with charcoal and recrystallized from chloroform to give 28.4 g of diol m.p. 119°: IR (nujol) 3380, 3250, 1650 cm$^{-1}$, NMR (DMSO-d$_6$) δ 3.6 (t, 2H), 3.8–4.3 (m, 3H), 4.7 (t, 1H), 5.1 (d, 1H), 7.5 (m, 4H), 8.2 (d, 1H); m/e 346.

Anal: Calculated for $C_{14}H_{12}Cl_2O_4S$: C, 48.43; H, 3.48; Cl, 20.42; S, 9.23. Found: C, 48.26; H, 3.44; Cl, 20.06; S, 9.15.

EXAMPLE 6

The product of Example 5 (10.44 g, 0.03 m) was suspended in 150 ml of acetic acid. To it was added chromic acid [17.88 g (0.06 m) Na$_2$Cr$_2$O$_7$.6H$_2$O in 81 ml H$_2$O+24 g H$_2$SO$_4$] dropwise over a period of 1 hour with the temperature at 40°–50°. The reaction mixture was allowed to stir for an additional hour, then diluted to 3 L with water. The solid was filtered, washed with water and dissolved in 1.2 L of ether. The ether was extracted with 5% of sodium bicarbonate. The solid which formed and the aqueous layer were acidified and extracted with ether. The ether layer after decolorizing with charcoal, drying and evaporation gave 4.5 g crude 3-[2,3-dichloro-4-(2-thienylcarbonyl)phenoxy] acetic acid (tricrynafen), m.p. 148°. Recrystallization from dichloroethane gave 3.7 g m.p. 150°–150.5°: IR (nujol) 1660, 1750 cm$^{-1}$, NMR (DMSO-d$_6$) δ 5.0 (s, 2H), 7.5 (m, 4H), 8.2 (d, 1H).

Anal: Calculated for $C_{13}H_8Cl_2O_4S$: C, 47.15; H, 2.43; Cl, 21.41; S, 9.68. Found: C, 47.38; H, 2.64; Cl, 21.46; S, 9.65.

EXAMPLE 7

A mixture of 0.746 g (0.006 m) of the cyclic carbonate from Example 4 and 20 ml of acetic acid is reacted with 1.79 sodium chromate hydrate, 16 g of sulfuric acid and 5.9 ml of water on the steam bath for 5 hours. The mixture was quenched and taken up in sodium bicarbonate solution. The mixture is acidified and extracted with ether. The ether extract was in turn extracted into sodium bicarbonate solution. Aqueous acid separates tricrynafen (0.039 g).

EXAMPLE 8

The product of Example 2 (11.9 g, 0.05 m) is heated with N,N-thiocarbonyldiimidazole (4.45 g, 0.025 m) in refluxing toluene for 30 minutes. The solution is cooled, washed with water, dried and evaporated to give 3-(2,3-dichlorophenoxy)-propanediol-1,2-thiocarbonate. This product is carried through the sequence described above to give tricrynafen.

EXAMPLE 9

The following oxidations were carried out at room temperature on the product of Example 5 to give ticrynafen. The reaction product was analyzed by comparative thin layer chromatography (t.l.c.).

A. Diol (0.347 g); manganese dioxide (3 g); acetone

B. Diol (0.347 g); potassium carbonate (1.189 g); sodium periodate (1.71 g); potassium permanganate (0.025 g); t. butanol C. Diol (0.347 g); potassium permanganate (1.589); 10% sodium hydroxide (10 ml).

What is claimed is:

1. The method of preparing ticrynafen comprising:
   A. exhaustively esterifying a compound of the formula:

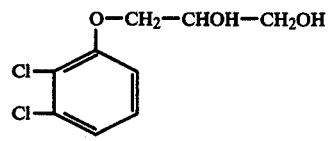

to give an ester compound of the formula:

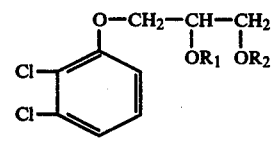

in which R$_1$ and R$_2$ are the same and are lower alkanoyl of from 1–5 carbons, carbomethoxy, carbethoxy or, when taken together, carbonyl or thiocarbonyl;

B. reacting said ester compound with thenoyl chloride or bromide under Friedel-Crafts conditions with an excess of 3–5 mole equivalents of a Lewis acid catalyst to give a diol ester compound of the formula:

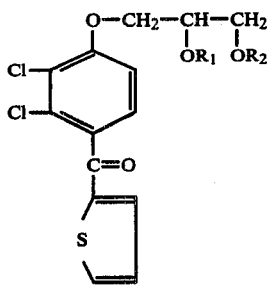

in which $R_1$ and $R_2$ are as defined above;

C. hydrolyzing said diol ester compound under acid or alkaline conditions to give a diol compound of the formula:

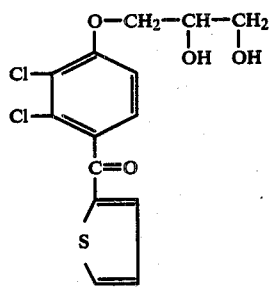

and D. oxidizing said diol compound with a diol oxidizing agent.

2. The method of claim 1 in which $R_1$ and $R_2$, when taken together, are carbonyl.

3. The method of claims 1 in which the Lewis acid catalyst in step B is aluminum chloride.

4. The method of claims 1 in which the esterifying agent is ethyl or methyl carbonate in excess.

5. The method of preparing compounds of the formula:

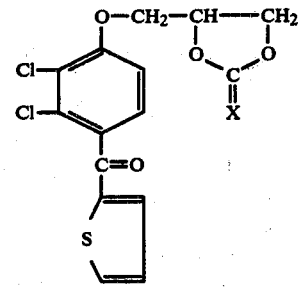

in which X is O or S; comprising reacting under Friedel-Crafts condition a compound of the formula:

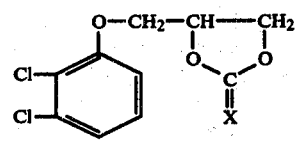

in which X is O or S; with thenoyl bromide or chloride in the presence of about 4 mole equivalents of aluminum chloride.

6. The method of claim 5 in which X is O and thenoyl chloride is the acylating agent.

7. The method of claim 6 in which methylene chloride is the solvent and the reaction is run at from room temperature to reflux temperature of the reaction mixture until the reaction is substantially complete.

* * * * *